United States Patent [19]

Lipps et al.

[11] 4,209,391
[45] Jun. 24, 1980

[54] APPARATUS AND METHOD FOR AUTOMATICALLY CONTROLLING HEMODIALYSIS AT A PRE-SELECTED ULTRAFILTRATION RATE

[75] Inventors: Bennie J. Lipps, Walnut Creek; Julian I. Landau, Concord, both of Calif.

[73] Assignee: Cordis Dow Corp., Miami, Fla.

[21] Appl. No.: 958,329

[22] Filed: Nov. 6, 1978

[51] Int. Cl.² .................... B01D 19/00; G05D 11/00; B01D 11/04
[52] U.S. Cl. .................................. 210/22 A; 210/188; 210/143; 210/321 B; 137/99
[58] Field of Search ............... 210/321 B, 97, 88, 188, 210/196.1, 143, 22 C; 417/25, 99, 251; 137/99

[56] References Cited

U.S. PATENT DOCUMENTS

| | | | |
|---|---|---|---|
| 4,008,003 | 2/1977 | Pinkerton | 417/251 |
| 4,037,616 | 7/1977 | Pinkerton | 210/321 B |
| 4,054,522 | 10/1977 | Pinkerton | 210/321 B |
| 4,085,046 | 4/1978 | Saporito, Jr. | 210/521 B |
| 4,113,614 | 9/1978 | Rollo et al. | 210/321 B |
| 4,118,314 | 10/1978 | Yoshida | 210/321 B |
| 4,119,113 | 10/1978 | Meginniss | 210/321 B |

*Primary Examiner*—Thomas G. Wyse
*Assistant Examiner*—E. Rollins Cross
*Attorney, Agent, or Firm*—Neal A. Waldrop

[57] ABSTRACT

Apparatus for and method of automatically controlling the quantity and rate of liquid removed from blood during hemodialysis. The apparatus supplies dialysate in a single pass system in a closed, controlled volume circuit which includes an above atmospheric pressure portion and a below atmospheric pressure portion. The above atmospheric pressure portion includes a pair of chambers for alternate supply to and removal of the dialysate from the below atmospheric pressure portion which contains an artificial kidney and a third means for removing fresh dialysate from the above atmospheric pressure portion; the below atmospheric pressure portion includes means which isolates the kidney containing portion and restores pressure to spent dialysate to a pressure at least equal to or higher than the pressure of the dialysate fed into said closed circuit; the above atmospheric circuit also includes means for removing gas from the spent dialysate prior to filling the spent dialysate removal chamber before discard.

13 Claims, 3 Drawing Figures

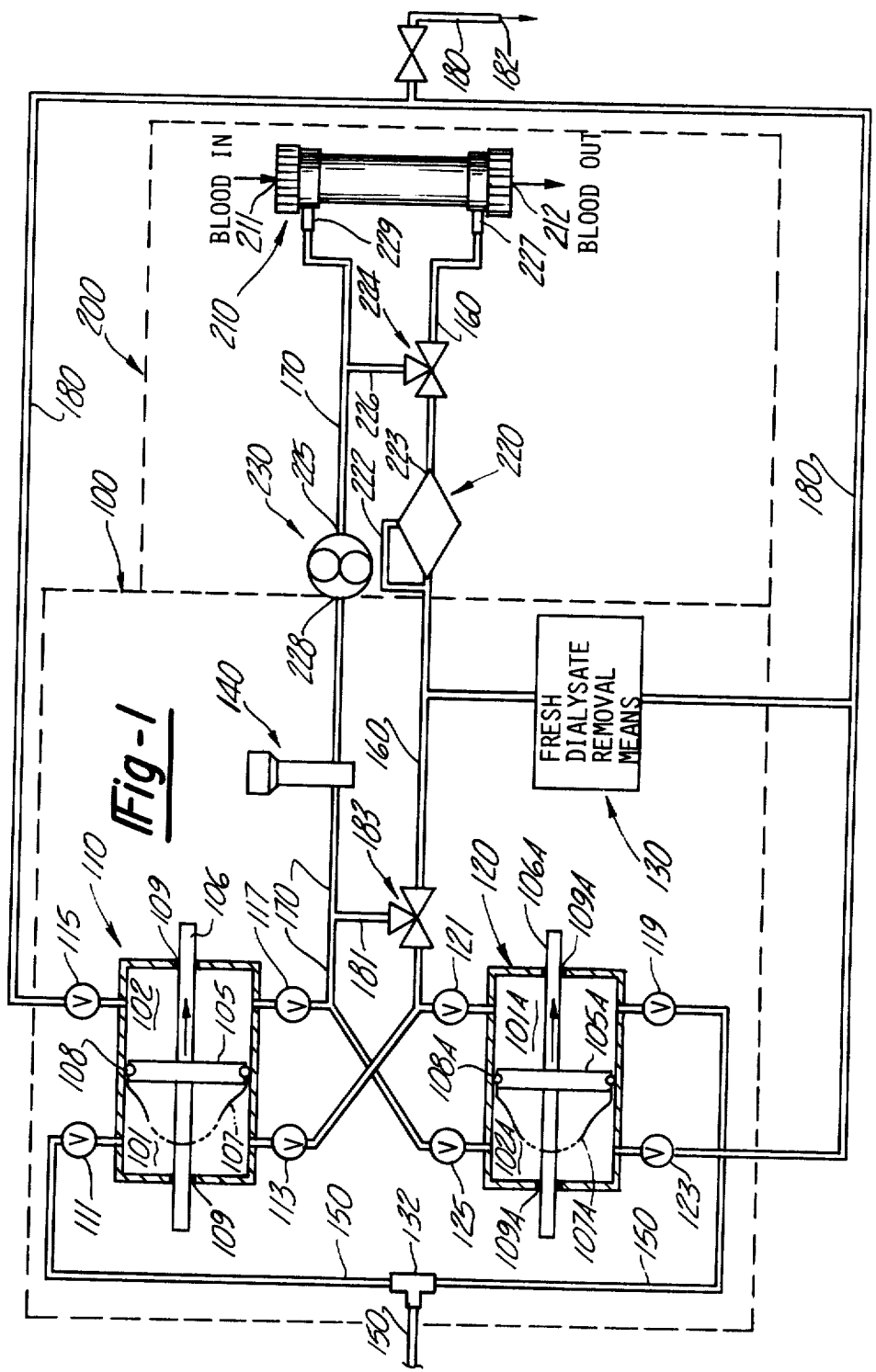

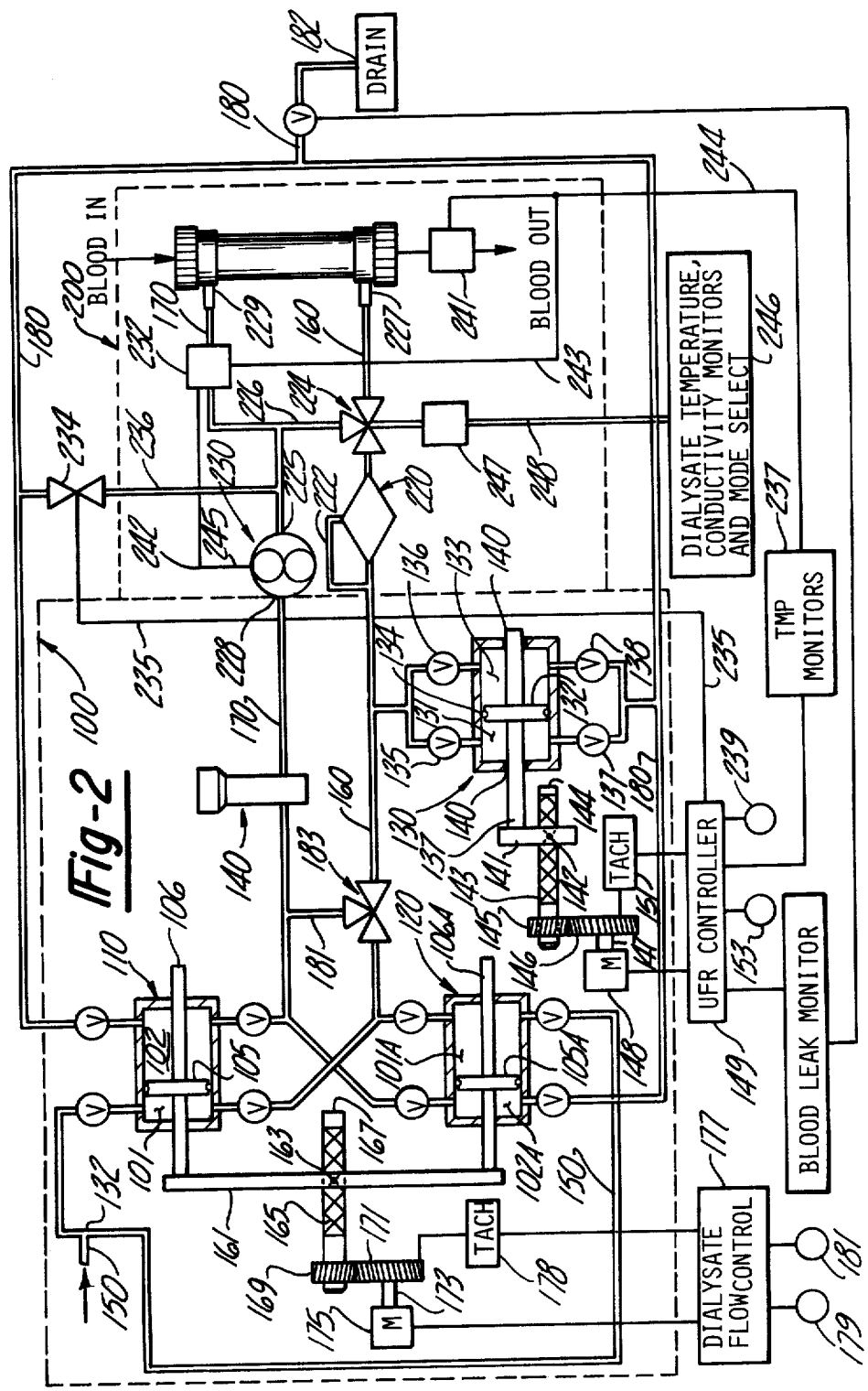

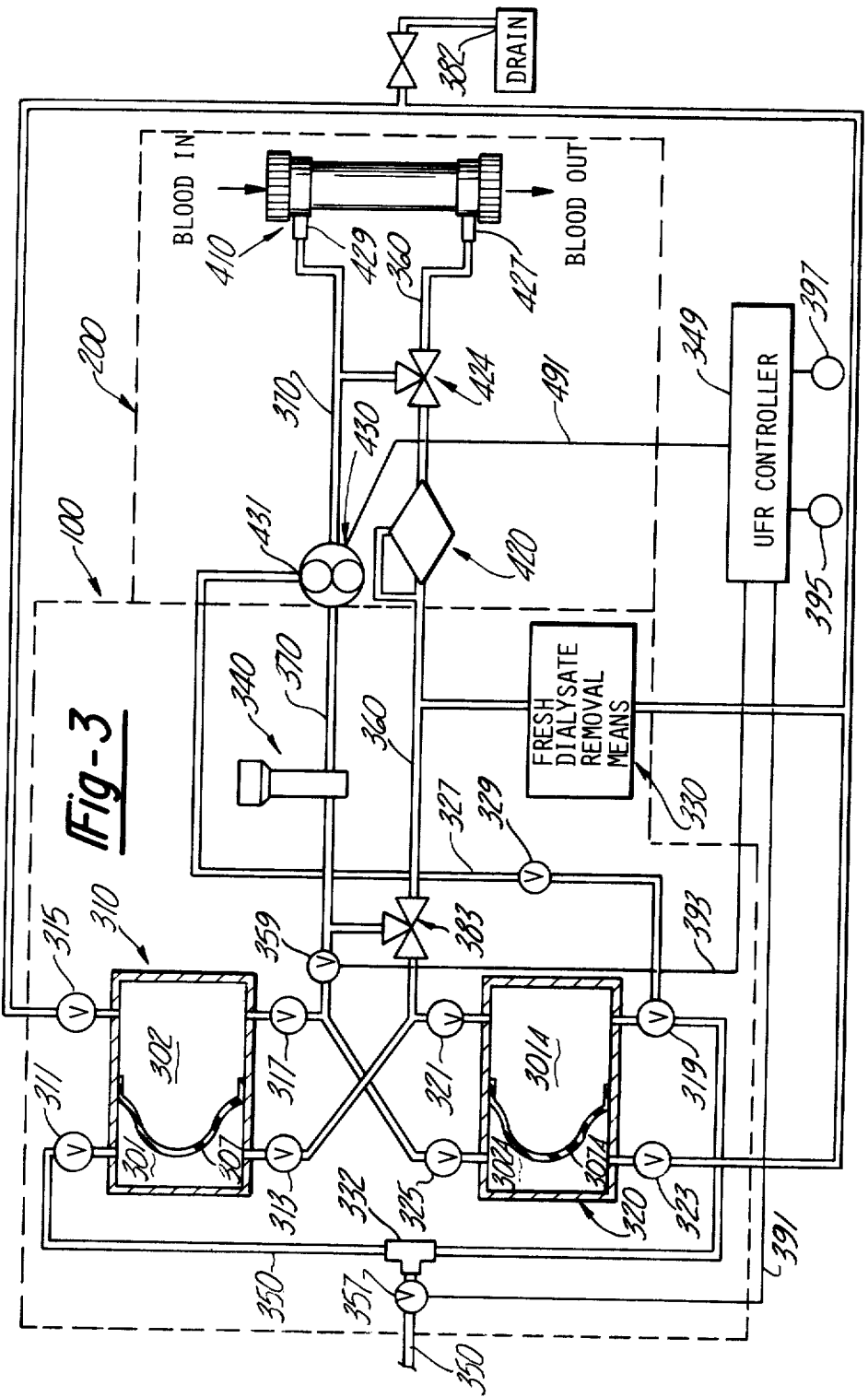

APPARATUS AND METHOD FOR AUTOMATICALLY CONTROLLING HEMODIALYSIS AT A PRE-SELECTED ULTRAFILTRATION RATE

BACKGROUND OF THE INVENTION

This invention relates to apparatus and a method which enables improved use of artificial kidneys in hemodialysis. More particularly, it concerns an improved dialysate circuit for separating liquid from blood at a precise pre-selected rate and quantity during hemodialysis, and a method which uses the improved apparatus and controls transmembrane pressure by control of the rate of liquid removal from the circuit.

The apparatus includes a closed, controlled volume circuit which incorporates improvement means that insure maintenance of the hydraulic, or liquid, integrity of the circuit sufficiently accurately to enable pre-selection of the desired ultrafiltration rate and maintenance thereof without physician or technician change of operating parameters throughout the entire hemodialysis treatment. These improvement means include piston and cylinder units for supply of dialysate to and from the kidney that resemble heretofore known units but in the preferred embodiment a pair of such units are herein combined with a third piston and cylinder control unit in a new manner and arrangement which provides a new method of operation and control of the hemodialysis treatment relative to heretofore clincally employed methods. The new method, and apparatus, in reliance on the improved, precise hydralulic integrity of the dialysate circuit, uses the third piston and cylinder unit to positively withdraw from that circuit the exact amount of liquid, or ultrafiltrate, which is equal to the excess water desired to be removed from the renal insufficiency patient being treated. Due to the positive withdrawal demand by the third piston and cylinder unit, pressures within the sub-atmospheric pressure portion of the circuit and most importantly the pressure differential between the blood and dialysate sides of the kidney, i.e., the transmembrane pressure, changes as a function of that demand and pressure isolation elements maintain that pressure irrespective of blood pressure changes, or downstream pressure changes on the dialysate. The result is an automatic changing of pressure across the membrane to the pressure which is required to ultrafiltrate water from the blood at the preset rate demanded and controlled by the operation of piston and cylinder unit.

Otherwise stated, the new method intentionally causes the transmembrane pressure to float to the subatmospheric pressure which will supply an ultrafiltration rate demanded by the operator-set liquid removal rate. Such method of operation basically differs from the clincially used prior method in which the physician or technician selected the initial transmembrane pressure and thereafter attempted to maintain that set transmembrane pressure throughout the four to six hour hemodialysis treatment by making periodic alterations responsive to observed excursions from the pre-set transmembrane pressure. It also basically differs from methods which employ positive pressure on the blood to attain the desired transmembrane pressure.

A most important advantage which results from the use of the new method, and apparatus, of this invention is that it provides precise removal of the desired amount of excess water from the patient, at the rate best suited to the requirements of the individual patient, and maintains the rate of that removal substantially uniform on a continuous, automatic basis. This result is achieved irrespective of changes which may occur, and normally do occur in the impedence across the semi-permeable membrane or hollow fiber wall surfaces, to liquid separation from the blood due to clotting or other blocking of the minute openings in the membrane, or to uncontrollable changes which may occur in the pressure on the blood side of the artificial kidney, and is therefore more precise and reliable than clincially used procedures that rely on the assumption that the artificial kidney will maintain throughout the entire hemiodialysis its designed, or new condition, $K_{UF}$, i.e., its ability to pass water as a function of transmembrane pressure.

The method of this invention, and the apparatus to enable its performance, differs from all known prior devices and methods even though this area of hemodialysis treatment has received an extensive amount of attention and research in the past. A review of prior attempts to measure ultrafiltration rate and volume in hemodialysis is below set forth as background basis for identifying the differences which characterize this invention.

As above suggested, prior clinical practice has made use of measurements of ultrafiltrate during hemodialysis by making manual changes to the pressure on the dialysate side of the membrane during the hemodialysis after periodic observation of instantaneous measurements of the quantity or rate of ultrafiltrate being removed. After making the change to a pressure considered corrective by the technician or operator the apparatus maintains the newly selected transmembrane pressure until it is later reset, as necessary. U.S. Pat. No. 3,990,973 shows such a system; it describes an ultrafiltration measuring system which interrupts dialysate flow to and from the kidney and during the interruption measures the ultrafiltrate being generated. The dynamic transmembrane pressure in the artificial kidney at the instant of interruption is maintained during the period required to measure the ultrafiltrate in a rotameter. After comparing the measured rate with the initially set rate, the difference is used as a guide to the operator in resetting the transmembrane pressure to a value intended to achieve the initial ultrafiltrate removal objective for the hemodialysis treatment.

Other patents which disclose means for collecting ultrafiltrate in a graduated cylinder, or its equivalent, during hemodialysis and control the process by making manual changes in the operating parameters which determine transmembrane pressure include U.S. Pat. Nos. 3,669,880, 3,969,069, 3,979,284, 4,021,341 and 4,093,545. Certain of these patents employ a closed recirculation circuit which includes the artificial kidney and employ a pair of pumps, or piston-cylinder means, or cylinders provided with diaphragms for supplying equal quantities of dialysate to and from the kidney and withdraws a portion of the spent dialysate into a measuring vessel. For example, U.S. Pat. No. 4,021,341 shows a system in which input and output pumps are linked to provide substantially equal volumes of dialysate to and from an artificial kidney and dialysate output in excess of dialysate input is separated and measured to thereby monitor the instantaneous rate of ultrafiltration and total ultrafiltration volume. The rate is measured in a rotameter, and after observation is used by the operator as the basis for manually changing the input dialysate attenuator setting and/or the output dialysate pressure amplifier setting to thereby change the transmembrane pressure as needed to control ultrafiltration rate. This system includes the inaccuracies inherent in pump operation and matching of pumped volumes over a four to six hour hemodialysis treatment; it also has the disadvantage of permitting recirculation of spent dialysate to the kidney and this recirculation decreases dialysis efficiency, or requires frequent manual inspection to prevent pressure attenuator settings that allow such spent dialysate recirculation.

U.S. Pat. No. 4,093,545 shows a dialysate supply chamber which supplies dialysate to an artificial kidney and recieves spent dialysate and ultrafiltrate from the kidney and provides a visible measuring tube to indicate the ultrafiltrate additions in the level of the dialysate storage chamber.

The article entitled "Clinical Evaluation of a Pre-set Ultrafiltration Rate Controller Available for Single Pass and Hemodiafiltration Systems", *Artificial Organs*, May, 1978, pp. 141–143, discloses for a single pass system the provision of dialysate to and from an artificial kidney by employing twin chambers outfitted with vertically oriented diaphragms. Removal of a certain amount of the spent dialysate in the closed system is stated to cause negative pressure to develop on the dialysate side of the membrane and resultant ultrafiltration of water through the membrane. This system includes a degasser in the spent dialysate line to remove gas from the withdrawn dialysate prior to its measurement.

The article entitled "The Accurate Control of Ultrafiltration", *Artificial Organs*, pp. 144–146, May, 1978, describes a pair of isovolumetric pumps in the form of two pistons mounted on a common shaft which reciprocate in chambers provided with valves and a switching system similar to that disclosed in U.S. Pat. No. 3,406,826 to thereby supply dialysate to, and remove spent dialysate from, an artificial kidney in a closed dialysis circuit; this circuit employs a peristaltic pump adjacent to the kidney to remove a portion of the spent dialysate which is collected in a visible graduated cylinder.

The dialysate flow control systems commercially available from Fluid Metering Inc., Oyster Bay, N.Y., which are designated F2MX and F4M2 employ a pump in an efferent line from an artificial kidney to withdraw spent dialysate from a closed system; in one of the possible modes of operation using pairs of cylinders fitted with pistons, or diaphragms, to supply dialysate to the kidney the slaved relationship between the pistons or diaphragms, imposes an ultrafiltration demand on the membrane. These systems measure withdrawn spent dialysate after degassing only the withdrawn fluid.

The importance of removing gas from fluids removed from blood which are being used to monitor the progress of a hemodialysis treatment is recognized in U.S. Pat. No. 4,054,522; that patent further recognizes that a major source of error in attempts to monitor dialysate volumes, particularly in single pass systems, has been the inclusion of gases in the circulating dialysate and that patent proposes to degas liquids in the apparatus therein described which uses reciprocating diaphragms in chambers having different volumes.

SUMMARY DESCRIPTION OF THIS INVENTION

The apparatus and method of this invention differs from and is not shown in any of the above described prior art, or other art or practices known to applicants. The apparatus differs by arranging twin, commonly driven, piston-cylinder units and a third independently powered unit of smaller volume than the twin cylinder units in a positive pressure circuit such that all three units are in the portion of the circuit which is separated from the negative to atmosphere pressure artificial kidney containing portion of the circuit. The third unit is preferably a piston-cylinder unit and is located in the above atmospheric pressure circuit portion in the infeed dialysate line and withdraws gas-free, fresh dialysate at above atmospheric pressure from the circuit when its power means is activated. It is separated from the kidney dialysate inlet by a pressure reducing means such as a back pressure regulator in a closed circuit such that negative pressure is developed on the dialysate in the kidney as a function of the rate of withdrawal of fluid by the third piston-cylinder unit. Additionally, the cylinder chamber in each of the twin piston-cylinder units that receives spent dialysate to be discarded is isolated from the below atmospheric pressure kidney portion of the circuit by a positive pressure pump which increases the pressure on the spent dialysate from the exit kidney pressure to a pressure at least as high as, and preferably higher than, the pressure on the in-feed dialysate; and most importantly a degasifier is located in the circuit between the high pressure side of the positive pressure pump and the inlet to the chamber in each of the twin piston cylinder units which receives spent dialysate for discard.

The improvement in this invention, which is not a part of the prior art, stems from the discovery that it is necessary to remove all gases which may enter the closed circuit in the sub-atmospheric pressure portion from all of the spent dialysate in order to achieve actual liquid integrity in a closed circuit.

In contrast, previous circuits of known prior art concentrated on degassing only the withdrawn spent dialysate and failed to recognize and deal with the entrained gas in the balance of the spent dialysate that is discarded in the next cycle. At efficient operating below atmospheric pressure conditions, for example, at numerically greater than negative 260 millimeters of mercury, substantial volume gas leaks occur due to poorly fitting connections; gas may also enter from the blood and from poorly degasified incoming dialysate; unless such gas is removed before the balance of the spent dialysate is returned to the cylinder receiving same for discard on the next cycle, liquid volumetric integrity is not maintained. To the extent that such gas occupies a portion of the volume of the spent dialysate chamber an error exists in the assumption that the withdrawn liquid, even after that withdrawn liquid is degassed, is precisely equal to the volume of water ultrafiltrated from the blood. The improved circuit of this invention eliminates this error and overcomes the problem, as will be explained in detail hereinbelow.

BRIEF DESCRIPTION OF THE DRAWINGS

FIG. 1 is a schematic illustration of the improved circuit of this invention;

FIG. 2 is a schematic illustration of the piston-cylinder preferred embodiment of this invention; and FIG. 3 is a schematic illustration of another preferred embodiment of the circuit of this invention using diaphragms in the cylinder units supplying dialysate to and receiving spent dialysate from the hemodialyzer portion of this circuit.

DETAILED DESCRIPTION OF THE METHOD AND PREFERRED EMBODIMENTS OF THE APPARATUS

As best seen in FIG. 1 the circuit comprises an above atmospheric pressure portion which includes the elements contained inside the portion of the circuit generally designated 100 and a below atmospheric pressure portion containing elements enclosed within the portion generally designated 200. The main components, or elements, of the circuit which remain at all times above atmospheric pressure include cylinder unit 110, cylinder unit 120, fresh dialysate removal means 130, and degasifier 140. The main components in the below atmospheric pressure portion 200 include the kidney generally designated 210, the pressure reducing means generally designated 220 and the pressure increasing means generally designated 230. These components are interconnected, as shown, by piping in a valved, closed, liquid-tight arrangement including fresh dialysate supply line 150, kidney dialysate supply line 160, spent dialysate removal line 170 and dialysate drain line 180.

The general scheme of operation of the circuit during hemodialysis is the provision of fresh dialysate from the above atmospheric pressure portion of the circuit to the kidney in the below atmospheric pressure portion and return of the spent dialysate from the kidney to the above atmospheric pressure portion of the circuit on an alternating time basis. Cylinder units 110 and 120 are interconnected with kidney 210 by valves which are actuated by a switching mechanism, not shown, such that only one of the cylinders is in fluid communication with kidney 210 at any instant in time. Cylinders 110 and 120 are divided into two chambers which permit the functions of cylinders 110 and 120 to alternate between half cycles in which one cylinder is filled with fresh dialysate as spent dialysate is being discarded, and concurrently the other cylinder is delivering fresh dialysate to the kidney as spent dialysate is being returned to the other chamber in that same cylinder. Whereas cylinders 110 and 120 alternate, fresh dialysate removal means 130, and presssure reducing means 220, are at all times in fluid connection with the cylinder chamber which is supplying fresh dialysate to kidney 210. Similarly, pressure increasing means 230 and degasifier 140 are at all times in fluid connection with the cylinder chamber which is receiving spent dialysate from kidney 210. For simplicity, the circuit including the cylinder 110 or 120 which is being filled with fresh dialysate as spent dialysate is expelled to drain will be hereinafter referred to as the fresh/drain circuit; the circuit including the cylinder which is supplying fresh dialysate to the kidney as spent dialysate is received from the kidney will be hereinafter referred to as the kidney/spent circuit.

Cylinder 110 is divided into chambers 101, 102 by means which reciprocate inside the bore of the cylinder. As shown in FIG. 1 in solid lines, the means is a piston 105 mounted on drive rod 106 and each is sealed with suitable sealing means such as O-ring 108 to isolate the fluid in chamber 101 from the fluid in chamber 102, and rod seal 109 to prevent fluid or air from entering or escaping from chambers 101 or 102. The cylinder dividing means satisfactorily or even preferably may be a diaphragm 107, as shown in phantom. Separate circuits which contain only pistons or diaphragms as the dividing means constitute preferred circuit arrangements which are more completely illustrated in FIGS. 2 and 3 respectively. Cylinder 120 is generally similar to cylinder 110 and corresponding parts thereof are designated with the same number with an A subscript.

Each of the chambers 101, 102, 101A and 102A of cylinders 110 and 120 respectively, are connected to fresh dialysate supply line 150, drain line 180, kidney dialysate supply line 160 and spent dialysate removal line 180 by valve means schematically represented in FIG. 1. Chamber 101 communicates with fresh dialysate line 150 through the off-on, two-way, valve 111 and with kidney dialysate supply line 160 through another two-way valve 113. Chamber 102 is connected to drain line 180 by two-way valve 115 and to spent dialysate removal line 170 by two-way valve 117. Chamber 101A is connected to fresh dialysate line 150 by two-way valve 119 and to kidney dialysate supply line 160 by two-way valve 121. Chamber 102A is connected to drain line 180 by two-way valve 123 and to spent dialysate removal line 170 by two-way valve 125. At the end of a stroke of the piston, or diaphragm, in cylinders 110 and 120, each of the valves is switched, or reversed, from an open to a closed position, or vice versa.

When cylinder 110 is in its half cycle to receive fresh dialysate in chamber 101 as piston 105 moves toward the right and to expel spent dialysate from chamber 102, the fresh/drain circuit comprises line 150 communicating with chamber 101 through open valve 111 and drain line 180 communicating with chamber 102 through open valve 115 while closed valves 113 and 117 isolate cylinder 110 from lines 160 and 170, respectively, and thus from kidney 210. During that same time, as piston 105 moves to the right, piston 105A in cylinder 120 also moves toward the right and cylinder 120 is in its half cycle to receive spent dialysate in chamber 102A and to expel fresh dialysate to the kidney from chamber 101A; the kidney/spent circuit comprises spent dialysate removal line 170 communicating with chamber 102A through open valve 125 and kidney/dialysate supply line 160 communicating with chamber 101A through valve 121 while closed valves 123 and 119 isolate cylinder 120 from drain line 180, and fresh dialysate line 150, respectively.

With the above described valving arrangment which isolates cylinders 110 and 120 from each other and the seals on piston 105 or diaphragm 107 isolate each chamber from the other, it will be seen that incoming fresh dialysate fills the same cavity from which spent dialysate was expelled and thus is identical in volume. Similarly, spent dialysate from kidney 210 fills the same cavity from which fresh dialysate was expelled into kidney 210 and that volume is identical; the same relationships apply in the other half cycle of the function of each cylinder. While it is desirable that the volume of cylinders 110 and 120 are substantially the same, it will be appreciated that the precise integrity of the fluid volume withdrawn by fresh dialysate removal means 130 being exactly the same volume of water, or ultrafiltrate, drawn from the blood and into the circulating dialysate is in no way affected by any difference in the volume of cylinder 110 from the volume of cylinder 120. Any such difference would merely cause a slight variation in the rate of dialysate flow through kidney 210 and such variations have little or no effect on the rate of ultrafiltration and little or no detectable effect on the clearance of urea, creatinine or other poisons from the blood during hemodialysis.

It is important to this inventon that the arrangement of cylinders provide separate chambers having valves capable of providing, on a time-alternating basis, the fresh/drain circuit and the kidney/spent circuit. However, it is unnecessary to provide separate inlet and outlet ports in each chamber 101, 102, 101A and 102A and a single inlet-outlet port in each chamber interconnected with three-way valves is preferred and generally less expensive to use. Since all valves reverse function at the end of a piston stroke, the most reliable and thus preferred valving construction is a single valve body or a pair of valve bodies containing the requisite number of valves and ports and each body responding to a single means operative to simultaneously reverse all of the valves. Suitable multi-valve constructions are commercially available from a number of suppliers in the United States and may be used. Such valve constructions offer the advantage of decreasing the possibility of malfunction, of timing delay in reversal of eight separate, solenoid-actuated, two-way valves of the type schematically illustrated in the drawings.

Fresh dialysate removal means 130 provides communication between drain line 180 and kidney dialysate supply line 160, which during practice of the method of this invention contains only fresh dialysate. Removal means 130 satisfactorily performs in an equivalent manner when located in spent dialysate line 170 between degasifier 140 and chambers 102 and 102A. Fresh dialysate, premixed and formulated to the desired composition and temperature, is supplied through fresh dialysate line 150 to a tee connection 132 at a pressure above atmospheric pressure in the range of about 1 to about 20 pounds per square inch, and preferably is supplied in the range of about 2 to about 7 pounds per square inch. Drain line 180 is open to the atmosphere at exit 182. Thus, the pressure on the fresh dialysate entering circuit portion 100 and exiting through means 130 remains above atmospheric pressure, unless the pressure is lowered due to other causes, which will now be further explained.

In the preferred circuit of this invention shown in FIG. 2, means 130 is a piston-cylinder unit having piston 132 sealed with O-ring 134 to separate the cylinder into isolated, fluid-tight chambers 131 and 133. Chambers 131, 133 are connected into kidney dialysate supply line 160 by valves 135 and 136, respectively, and connected to drain line 180 by valves 137 and 138, respectively. Piston 132 is reciprocated between the ends of cylinder means 130 by drive rod 139 which is integrally attached thereto and moves back and forth in seals 140. Rod 139 is rigidly connected to arm member 141 having protruding pawl 142 which follows spiral grooves 143 cut into the peripheral surface of rotatable rod or lead screw 144. Rod 144 is driven by the teeth of gear 145 meshing with teeth on drive gear 146 mounted on drive rod 147 of motor 148. If desired, means 130 may be pump means; where pump means is used a gear pump, or other positive pressure inducing means preferably having the capability of adjustment to pump micro-, or small volumes accurately should be selected. One suitable pump means for this purpose is described in U.S. Pat. No. 4,008,003. Upon actuating motor 148, which is schematically shown in FIG. 2 connected to UFR controller 149 by, for example, adjusting the power to the desired rotation rate indicated by tachometer 151 and displayed on the control surface of controller 149 as a visible read-out, illustrated at 153, or r.p.m. or milliliters per minute, the rotation of drive rod 143 causes pawl 142 to move piston 132 to the end of a stroke and reverse direction when pawl 142 reverses at the end of spiral groove 143 on lead screw 144; with valves 135 and 138 in the open position, and valves 136 and 137 closed, fresh dialysate is pulled, or sucked, from kidney dialysate line 160 into chamber 131 while fresh dialysate is expelled to drain line 180. At the end of each traverse of piston 132 to an end of cylinder 130, the valves reverse responsive to means such as conventional limit switches, or their equivalent, not shown. During the succeeding traverse the other chamber withdraws fresh dialysate from line 160 to fill chamber 133 and expel to drain the dialysate in chamber 131. Thus, the quantity withdrawn is directly controlled by the rate of movement of piston 132.

In a closed circuit, that is, a piping arrangement without liquid leaks at any of its connections, as illustrated, the withdrawal of liquid tends to reduce the pressure on the remaining fluid in the system. In the circuit of FIG. 1, in the absence of back pressure regulator 220 and positive pressure pump 230, withdrawal of fresh dialysate would reduce the pressure on the dialysate throughout the entire circuit. Such reduction is beneficial in the kidney to assist in creating, at least partially, the needed transmembrane pressure across the semipermeable membrane in the hemodialyzer, illustrated as a hollow fiber artificial kidney 210 in the drawings. It is to be appreciated that the benefits of this invention are attained when any of the other known hemodialyzers including coil or flat sheet types are employed. On the other hand, such a pressure reduction is undesirable in the circuit elements other than the hemodialyzer because the closed circuit loses its initial liquid tight characteristics as a function of the numerical increase of pressure negative to atmospheric pressure.

It has been observed that connections in the piping, in valves, seals and joints become a source of gas leaks into the circuit as the negative pressure increases, and practically speaking, the closed circuit is no longer liquid tight at negative pressures exceeding about $-200$ to about $-250$ millimeters of mercury. Air or gas which enters the closed circuit appears ultimately in the spent dialysate as bubbles and displaces a portion of the volume of liquid within the closed circuit downstream of the hemodialyzer; to the extent that air, or gas, occupies a portion of the interior volume of chamber 102 or chamber 102A instead of liquid spent dialysate prior to sending that spent dialysate to drain, the ultrafiltrate, or water, separated from blood in the kidney will be less than the fresh dialysate withdrawn by means 130 and to the same extent, or volume. In accordance with this invention, the expectation that the withdrawn liquid is precisely equal to ultrafiltrate is attained and the problem of the erroneous assumption resulting from failure to eliminate gas from the entire quantity of spent dialysate before returning it to the metering chamber for either recirculation, or discard, is overcome. Pressure isolating elements or components 220 and 230 and degasifier 140 solve the problem; pressure reducing means 220 prevents the lower pressure resulting from withdrawal of fresh dialysate to exist in circuit portion 100 and is suitably a commercially available back-pressure regulator having a conventional bypass loop 222. The resultant lower pressure does exist in the lines and elements in those lines, between the kidney side 223 of back pressure regulator 220 and the kidney side 225 of pressure increasing means 230 and at kidney inlet port 227 and kidney outlet port 229.

As shown in FIG. 1 these elements include only the artificial kidney 210, by-pass valve 224 and means 230. Valve means 224 includes valves in kidney dialysate supply line 160 and by-pass line 226 operative to stop flow toward the kidney and shunt it through line 226 and toward means 230. Pressure increasing means 230 is any means capable of receiving spent dialysate flowing in line 170 from kidney outlet 229 and raising the pressure of that fluid to a pressure above atmospheric from its incoming pressure which may approach negative 700 millimeters of mercury. Gear pumps or other commercially available positive pressure pmups, are suitable if capable of pumping fifty to about 750 millileters per minute of spent dialysate and inducing a positive pressure on the exit side 228 in the range of about 3 to about 25 pounds per square inch above atmospheric pressure. Under typical operating conditions for pump 230 in hemodialysis using the circuit of this invention, the pump receives spent dialysate at entry 225 in a pressure range of 200 to about 650 millimeters of mercury negative and converts the pressure to about 7 to about 12 pounds per square inch above atmospheric pressure at exit 228.

As shown in the preferred circuit in FIG. 2 additional elements in the below atmospheric circuit include spent dialysate pressure measuring means 232, typically a commercially available transducer, and relief valve 234 mounted in line 236 connecting spent dialysate line 170 into drain line 180. Valve 234 functions to quickly reduce transmembrane pressure in the event it becomes desirable during hemodialysis to speedily terminate ultrafiltrate separation from the patient's blood; in such event UFR controller 149, typically a microprocessor, is programmed to signal valve 234 through line 235 to open and pass dialysate to drain line 180 in sufficient quantity to quickly lower the transmembrane pressure to zero, as measured instantaneously and supplied to the microprocessor 149 by TMP monitor 237. Monitor 237 measures the transmembrane pressure constantly and displays same on display means 239 on the face of UFR controller 149, by determining the difference between spent dialysate pressure at transducer 232 and the venous blood pressure as measured by blood pressure measuring means 241, typically a gauge or transducer, and feeds that difference to TMP monitor 237 through lines 243, 244, respectively.

Positive pressure pump 230 may satisfactorily operate at a rate set at the beginning of the treatment to raise the pressure of spent dialysate in the range of about 2 to about 10 pounds per square inch above the pressure on the fresh dialysate entering the circuit at tee 232. On occasion it is desirable to change the pressure differential generated by pump 230 and automatic means for this purpose includes input from pressure transducer 232 to UFR controller through lines 243, for comparison to a preprogrammed maximum limit of negative pressure relative to normal operating speed of pump 230. When such limits are exceeded controller 149 signals means, not shown, through line 245 to speed up or slow down the rate of rotation of positive pressure means 230 to maintain pressure on the spent dialysate at exit 228 within the preset limits. The increased pressure on the spent dialysate generated by pump 230 serves to dissolve gas bubbles in that dialysate which may have entered in the below pressure circuit portion 200. Since the exit 228 pressure is maintained at a pressure at least as high as the in-feed dialysate and usually at a higher positive pressure the spent dialysate contains no dissolved gas above the quantity that may have been present in the in-feed dialysate which enters circuit 100 at a pressure in the range of about 2 to about 10 psi above atmospheric. The in-feed dialysate is premixed, formulated and raised to 37° C.±4° C. before entering circuit 100, and in the event the composition or temperature falls outside the preset limits, monitors in means 246 signal valve control means 247 and valve means 224 through line 248 to close the valve in line 160 and open the valve in line 226 to by-pass kidney 210.

Pump 230 functions in coopration with degasifier 140 to provide the pressure above atmospheric required to make the gas bubble separation effective and to insure that the spent dialysate being returned to metering chambers 102 or 102A is free of undissolved gases. Degasifier 140 is suitably an air trap of conventional type used in prior dialysate supply modules or devices, and preferably is adjustable to enable control of the pressure on the layer of air above the spent dialysate pool therein, if needed. Means for monitoring the pressure on such air layer by using microprocessor 149 to compare a preset range with the measured instantaneous pressure and signal means to adjust the liquid level inside air trap 140 to attain the preset pressure comprises means, not shown, which satisfactorily automates bubble removal and insures attainment of a preset maximum percent deviation between predicted ultrafiltrate separation from the blood and actual removal of ultrafiltrate.

As shown in FIG. 2, cylinders 110 and 120 are provided with a common drive means for piston rods 106, 106A, respectively, which is generally similar to the independent drive means for fresh dialysate removal means 130 described above. Piston rods 106, 106A, are rigidly connected to common drive beam 161 having centrally located pawl follower 163 which follows in spiral grooves 165 located on the periphery of even feed lead screw 167. Lead screw 167 is rotated by the meshing of the teeth on gear 169 with the teeth on drive gear 171 which is attached to drive rod 173 and driven by motor 175. Motor 175 is controllable by dialysate flow control 177 to a desired rotational speed measured by tachometer 178 and displayed on visual printout 179 in terms of revolutions per minute and in printout 181 in terms of milliliters per minute of fresh dialysate flow. The direct mechanical drive arrangement employed in the embodiment of FIG. 2 advantageously insures simultaneous travel of pistons 105 and 105A in cylinders 110 and 120, respectively, and more importantly, insures that those pistons arrive at the same precise instant at the end of each cylinder such that mechanical actuating means for simultaneously signaling the valve reversal is assured. Such valve actuating sensors may be located on the pistons themselves or on means attached to the piston rods or, preferably, take the form of a single arm member, or finger, attached to common drive beam 161. The use of single body, multiple valve constructions actuatable by contact of a single mechanical arm or finger member has been found to be highly advantageous and desirable to employ in commercial embodiments of the apparatus of this invention.

As may be seen in FIGS. 1–3, the kidney dialysate supply line 160 is connected to spent dialysate removal line 170 at a location within the above atmospheric pressure portion 100 by a by-pass line 181. Line 181 is connected into kidney dialysate supply line 160 by a three-way by-pass valve generally designated 183 containing valves normally open to flow of fresh dialysate in line 160 and closed to cross-flow in by-pass line 181. When desired, the circuit of FIG. 103 may be operated to ultrafiltrate water from blood in hemodialyzer 210 without concurrently removing poisons from the blood such as urea, creatinine, etc. This is accomplished by closing the valve in fresh kidney dialysate supply line 160 and opening the valve to allow recirculation of dialysate through by-pass line 181. During this mode of operation positive pressure pump 230 pumps the dialysate in the recirculating path comprising the degasifier 140, by-pass 183, fresh dialysate removal means 130, back pressure regulator 220 and by-pass valve 224. Valve 224 is set such that the valve in line 160 is closed and the valve in by-pass line 226 is open.

This recirculation mode of operation of the circuit controls transmembrane pressure automatically by controlling the rate of removal of fresh dialysate from removal means 130. The recirculation circuit also includes the same key elements for isolating the low pressure portion of the circuit from the above atmospheric pressure portion as in the dual function circuits described above; it includes pressure increasing means 230 and degasifier 140 to insure bubble removal and back pressure regulator 220 for isolating kidney 210 low pressures from the higher pressure on the valves and seals of dialysate removal means 130. It will be apparent that this mode of operation is an economic mode of operation when it is desired to ultrafiltrate, only, the blood of a patient for a portion of the contemplated treatment or the entire ultrafiltration portion of the blood purification treatment before subsequent separate removal of the normal poisons therefrom; it saves dialysate make-up costs and heat costs for the entire period of the ultrafiltration-only mode of operation.

In the preferred embodiment shown in FIG. 3, the circuit comprises an above atmospheric portion 100 and a below atmospheric portion 200 containing substantially the same elements or components shown in FIG. 1. Corresponding parts in the above atmospheric portion 100 have been numbered with 300 series numerals corresponding in their last two digits to the corresponding numbers in FIG. 1 and the components in portion 200 of the circuit have been given 400 series numerals corresponding in their last two digits to the corresponding numbers in FIG. 1.

The main difference between the embodiment shown in FIG. 3 and that shown in FIG. 2 is that the dividing means in cylinders 310 and 320 are diaphragms 307 and 307A, respectively, which separate the cylinders into separate fluid tight chambers as shown. These diaphragms are powered by different means than the common drive mechanism for pistons 105 and 105A which are described above in the detailed description of the circuit of FIG. 2. Diaphragms 307 and 307A are floating diaphragms which move inside the cylinders as a result of pressure on the incoming dialysate fluid from line 350 which enters chamber 301 or 301A in alternate half cycles; in the other half cycle, the driving force which causes movement of diaphragms 307, 307A, is pump 430 which causes flow of spent dialysate into chambers 302, 302A, alternately. The fluid pressure on the diaphragms during each half cycle must be controlled as closely as possible to effect similar rates of traverse, or reciprocation, of the diaphragms in cylinders 310 and 320 in order to enable simultaneous activation of the valves associated with each chamber at the end of diaphragm traverse to the end of its cylinder. It will be appreciated that unless both of the diaphragms have traversed to the end of their stroke before all eight of the valves are simultaneously reversed that flow will occur in lines and directions which are undesirable and which do not follow the flow paths outlined above in connection with the operation of the apparatus of FIG. 2. The apparatus of FIG. 3 includes means which enable the control of positive pressure pump 430 relative to the flow rate induced by the pressure on in-feed dialysate which includes flow rate measuring means 357, which measures the rate of in-feed dialysate flow, and flow rate control means 359 in spent dialysate removal line 370 which measures the rate of flow of the dialysate powered by the rotation of positive pressure pump 430. Each of valves 357 and 359 are connected to UFR controller 349, or micro processor, as above described, by lines 391 and 393, respectively. UFR controller 349 displays the instantaneous rates of flow as measured by flow rate measuring means 357 on visible printout 395 and the instantaneous flow rate as measured by flow rate controller 359 on visible printout 397. Micro processor 349 is preprogrammed to include calibration data for comparison with the instantaneous flow rate difference between that measured by means of 357 and 359 and to provide signals suitable to cause a change in rotation speed of positive pressure pump 430 to equalize the flow rates in in-feed dialysate line 350 and spent dialysate line 370.

The circuit shown in FIG. 3 provides line 329 for supplying a quantity of fresh dialysate to the in-feed side at 431 of positive-pressure pump 430 to prime that pump when the circuit is initially started. Unlike the circuit shown in FIG. 2 in which flow of dialysate into and from the kidney is powered by, and controlled by, the rotation of motor 175 which reciprocates pistons 105, 105A diaphragms 307, 308A provide no motive powers to the flow of dialysate, as above suggested. At start up, valves 319 and 329 are opened prior to initiating rotation of pump 430 to effect priming and commence flow of dialysate in the kidney/spent circuit.

The following examples show the effect of air leaks using the piston-cylinder apparatus of this invention without pressure isolation from the kidney and demonstrate the increasing degree of error with increasing negative pressure, the effects of positive pressure on the spent dialysate and the effects of positive pressure coupled with gas removal from the spent dialysate before it is returned to the metering chamber of the spent dialysate removal cylinder.

EXAMPLE 1

Laboratory tests were run using the piston-cylinder units shown in FIG. 2 in the identical piping arrangement except for the absence of the pressure reducing means 220, the pressure increasing means 230 and gas removal means 140. The tests employed three commercial artificial kidneys of the hollow fiber type available from Cordis Dow Corp., Concord, Calif., in three separate tests. In lieu of blood, a 50 milliliter graduated burette was filled with water and after purging air from the artificial kidney and capping the upper blood port 211, the burette was attached to the bottom kidney port 212. Piston-cylinder units 110 and 120 were operated to supply approximately 500 milliliters per minute of dialysate to the kidney at an incoming pressure of approximately 5 pounds per square inch above atmospheric pressure. Dialysate withdrawal piston-cylinder 130 was than started by actuating motor 148 and setting tachometer 151 to a first setting. The volume of cylinder 130 in these tests was 4 milliliters and the settings were arbitrarily selected at an increasing number of revolutions of motor 148 to increase the rate of reciprocation of piston 132 to fill and expel chambers 131 and 133, alternately.

The tests involved making an adjustment to the desired tachometer setting and allowing the system to stabilize at the negative pressure caused by removal of water from means 130; this was accomplished by observing the pressure on a pressure gauge located at the location of pressure transducer 232 in FIG. 2. Such stabilization usually requires about 8 to 12 minutes and the stabilized pressure was then recorded. When the pressure stabilized, at an end of the stroke of piston 132, the time and water level in the burette was observed and recorded and a stop watch was started. Five full cycles of piston 132 traverse, each traverse being one cycle, were observed and at the end of the fifth cycle was calculated by subtracting the actual milliliters from the predicted milliliters per minute and dividing the difference by the predicted milliliters per minute; the results of these calculations are recorded in Table I in the column headed % Dev.

As above indicated, the artificial kidney used in the recorded test in the left-hand column of Table I was commercially designated C-DAK TM -5, which is a hollow fiber artificial kidney containing a sufficient number of small, semi-permeable, cellulose hollow fibers to provide a nominal surface area of 2.5 square meters; in the middle column, the artificial kidney used was commercially designated C-DAK TM -7, which contains a sufficient number of semi-permeable, cellulose, hollow fibers to provide a nominal surface area of 1.8 square meters; and in the righthand column, the artificial kidney used was commercially designated C-DAK TM -8, which is a hollow fiber artificial kidney containing a sufficient number of small hollow, semi-permeable, cellulose acetate fibers to provide a nominal surface area of 0.9 square meters.

TABLE I

| Kidney Pressure Mm. Hq. Neg. | C-DAK TM - 5 | | | C-DAK TM - 7 | | | C-DAK TM - 8 | | |
|---|---|---|---|---|---|---|---|---|---|
| | UFR Pred. ML/MIN. | UFR Actual ML/MIN. | % Dev. % | UFR Pred. ML/MIN. | UFR Actual ML/MIN. | % Dev. % | UFR Pred. ML/MIN. | UFR Actual ML/MIN. | % Dev. % |
| −25.4 | — | — | — | 11.49 | 10.26 | +11 | — | — | — |
| −38.1 | — | — | — | — | — | — | 2.49 | 3.55 | −43 |
| −55.9 | — | — | — | 13.25 | 11.72 | +12 | 2.53 | 3.64 | −44 |
| −76.2 | — | — | — | — | — | — | 5.48 | 5.75 | −5 |
| −88.9 | — | — | — | 14.60 | 12.70 | +13 | — | — | — |
| −96.5 | 8.30 | 6.93 | +17 | — | — | — | — | — | — |
| −111.7 | — | — | — | — | — | — | 7.28 | 7.49 | −3 |
| −114.3 | — | — | — | — | — | — | 7.31 | 6.85 | +6 |
| −127.0 | 11.30 | 9.66 | +15 | — | — | — | — | — | — |
| −134.6 | — | — | — | — | — | — | 9.88 | 9.15 | +7 |
| −149.8 | — | — | — | 17.70 | 14.78 | +16 | — | — | — |
| −157.5 | — | — | — | — | — | — | 11.85 | 10.5 | +11 |
| −162.6 | 14.37 | 12.33 | +14 | — | — | — | 13.17 | 11.53 | +12 |
| −177.8 | — | — | — | — | — | — | 14.42 | 11.60 | +20 |
| −190.5 | — | — | — | — | — | — | 17.32 | 14.38 | +17 |
| −193.4 | — | — | — | 20.62 | 16.50 | +20 | — | — | — |
| −216 | — | — | — | — | — | — | 21.01 | 16.17 | +23 |
| −238.7 | — | — | — | 22.99 | 17.93 | +22 | — | — | — |
| −248.9 | 29.70 | 18.72 | +37 | — | — | — | — | — | — |
| −279.4 | — | — | — | 25.64 | 19.49 | +24 | — | — | — |
| −287.0 | — | — | — | 28.17 | 20.14 | +29 | — | — | — |
| −289.6 | 36.7 | 22.1 | +40 | — | — | — | — | — | — |
| −309.9 | — | — | — | 30.30 | 20.75 | +32 | — | — | — | the new water level in the burette, and the time were recorded. This procedure was repeated at new and higher settings of the tachometer to thereby create faster rates of movement of piston 132, higher rates of water removal and higher negative pressure. The number of settings and results of each test are set forth in Table I. In Table I, the pressure on the dialysate in the kidney is recorded in milliliters of mercury negative, i.e., below atmospheric pressure.

The volume of the bore of the cylinder in dialysate removal means 130 of 4.0 milliliters was used as the basis of calculations comparing the quantity of dialysate predicted to be removed with the quantity actually removed, in reported terms of rate of removal in milliliters per minute; these numbers are recorded in Table I in the columns designated UFR Pred.-ML/MIN. and UFR Actual-ML/MIN. At 100% accuracy, 20 milliliters of dialysate would be pulled into the kidney from the burette and would pass through the hollow fibers in the kidney and be delivered to the dialysate drain line 180. For comparison the percent deviation between the predicted rate of removal and the actual rate of removal From the results of the tests shown in Table I, it may be seen that as the kidney negative pressure numerically increases, the difference between the quantity of ultrafiltrate actually removed relative to the predicted filtrate removed increases; the maximum percent deviation occurred in the kidney having the greatest surface area, and the largest number of hollow fibers. It has been observed that increasing negative pressure increases the likelihood of leaks of air into the circuit at ports on the kidney, at valves in the piston-cylinder units when at negative pressure, and due to secondary deaeration, i.e., bubble formation from dissolved air in the incoming dialysate, or from blood. It may also be observed from Table I that the percent deviation exceeded about 20% at pressures above about 200 millimeters of mercury negative to atmospheric pressure. Although operating results differ somewhat from clinic to clinic performing intermittent hemodialysis treatments using artificial kidneys which are operated by the usual technician-adjusted transmembrane pressure during the treatment, an average percent deviation falls in the range of about 15 to about 20% when dialysate pressures are in the ordinarily used range varying from about minus 200 to about minus 500 millimeters of mercury negative to atmospheric pressure during the treatment. Thus, it is apparent that the circuit used in the tests represented by the data included in Table I gives less accurate ultrafiltration control than present day clinically used procedures of conducting hemodialysis using hollow fiber kidneys and the normally employed procedures during the manual transmembrane pressure adjustment treatment.

EXAMPLE 2

A test was performed using the circuit of Example 1, modified to include pressure increasing means 220 in the form of a conventional back pressure regulator, and pressure increasing means 230 in the form of a positive pressure pump; thus, the circuit was identical to FIG. 2 but did not contain degasifier 140. Positive pressue pump 230 was operated at a speed to produce an average pressure on the spent dialysate exiting from high pressure side of about 10 lbs/sq. inch. The incoming dialysate to the circuit at tee 132 was at approximately 5 lbs/sq. inch above atmospheric pressure.

The test was performed using the same procedures described above in Example 1 except that the speed settings of tachometer 151 were such as to produce negative pressures in the kidney numerically greater than 200 millimeters of mercury and extending to negative pressure exceeding those normally encountered in hemodialysis treatments performed in modern, efficiently operated clinics in the United States which only rarely exceed negative 600 millimeters of mercury.

This test used a commercial hollow fiber artificial kidney commercially available from Cordis Dow Corporation under the designation C-DAK TM -4 which provides a nominal surface area of 1.3 sq. meters of cellulose fibers, and the results are shown in Table II. From those results it will be apparent that the addition of the back pressure regulator and a positive pressure pump in the circuit of FIG. 2 made it possible to operate at negative pressures slightly exceeding 500 millimeters of mercury negative to atmospheric pressure before the percent deviation exceeded 20%, as compared to the circuits tested in Example 1 which produced a 20% deviation at pressures of approximately 200 millimeters mercury negative to atmospheric pressure. The improvement is thought to result from the maintenance of above atmospheric pressure on the valves and seals in the dialysate supply piston cylinder units 110, 120 and the fresh dialysate removal piston cylinder unit 130; it is partially due to dissolving at least some of the air bubbles which enter the circuit as the result of raising the pressure in positive pressure pump 230 to approximately 10 psi as it enters the above atmospheric pressure portion of the circuit 180 and before the fluid in line 160 is returned to the receiving chamber 102, 102A alternately.

TABLE II

| | C-DAK TM - 4 | | |
|---|---|---|---|
| Kidney Pressure MM. Hq. Negative | UFR Predicted ML./MIN. | UFR Actual ML./MIN. | % Deviation |
| −215.9 | 5.75 | 5.46 | +5 |
| −381.0 | 11.9 | 10.6 | +11 |
| −546.1 | 20.8 | 16.5 | +21 |
| −660 | 30.8 | 20.3 | +34 |

EXAMPLE 3

A test was run using the identical circuit shown in FIG. 2. Relative to the tests of Example 2 the circuit was modified to include an air trap 140 of conventional design.

The kidney used in this test was a commercial C-DAK TM -4 artificial kidney from the commercially available stock of Cordis Dow Corp. The test was conducted by using the same procedures and methods of calculation of the percent deviation that were used in Examples 1 and 2, and the results are reported in Table III. From the results set forth in Table III it is apparent that the circuit of FIG. 2 produces significantly improved conformance of the actual liquid delivered through withdrawal piston-cylinder 130 to the predicted quantity. This conformance extended over the pressure range between about 200 millimeters mercury to about 650 millimeters mercury negative to atmospheric pressure. The percent deviation reached a maximum of about 11-12 percent at the highest negative pressure tested and shows that adding air trap 140 in the circuit, as shown, greatly improves the precision of untrafiltrate generation and reduces the error attributable to bubbles and air in the fluid in the spent dialysate line 160 which is returned to the receiving chamber 102, 102A of the dialysate removal piston-cylinder units 110, 120. The results obtained represent a substantial improvement over those ordinarily obtained in clinics in the United States which employ manual adjustments of transmembrane pressure, the best known procedure prior to this invention.

TABLE III

| | C-DAK TM - 4 | | |
|---|---|---|---|
| Kidney Pressure MM. Hq. Negative | UFR Predicted ML./MIN. | UFR Actual ML./MIN. | % Deviation |
| −190.5 | 5.97 | 6.38 | −8 |
| −241.3 | 8.9 | 8.31 | +7 |
| −304.8 | 12.2 | 11.0 | +10 |
| −406.4 | 15.3 | 13.6 | +11 |
| −647.7 | 21.0 | 23.30–23.6 | +11-12 |

Example IV

Clinical evaluations of the circuit shown in FIG. 2 were made at two hospitals using artificial kidneys designated C-DAK TM -5 and C-DAK TM -7, identified above. In the first evaluaton five hemodialysis treatments on four intermittent dialysis patients were conducted, three treatments using the C-DAK TM -7 artificial kidney and two treatments using the C-DAK TM -5 artificial kidney.

The conditions employed in the five hemodialysis treatments at clinic No. 1, the results of which are included in Table IV-A, included provision of fresh dialysate warmed to about 37° C. at a pressure of about 5 pounds per square inch above atmospheric pressure at about 500 milliliters per minute, and an average blood flow rate of 230 milliliters per minute.

The treatments required from three and one half to four and one half hours with an average of about 4 hours. Predicted water removal was based on a microprocessor summation of the fresh dialysate sent to drain by piston-cylinder unit 130, reported on remote UFR control 153 onthe front face of the apparatus housing the circuit of FIG. 2 as a visible print out from the microprocessor, as explained above. The actual water loss recorded in Table IV-A was based on the difference in the weight of the patient immediately prior to start-up and immediately after completion as measured on both upstanding balance scales and bed scales, after taking into account liquid loss or gain by the patient from intake or excretion during the treatment. Calculated percent deviation is reported as percent deviation from actual weight loss and was calculated by subtracting actual loss in grams for the entire treatment from predicted total grams and dividing by actual loss, and where actual exceeded predicted the percent deviation is reported as negative, as in Examples 1-3.

The conditions employed at clinic No. 2 were similar to those described for clinic No. 1 except that the trial consisted of four treatments on three patients, all using a C-DAK ™ -7 model artificial kidney. Blood and dialysate flow rates are shown in Table IV-B; actual weight loss for patients 1, 2 and 3 was based on balance scale weights while for patient 4 the loss was based on bed scale weight. Percent deviation was calculated in the same manner used in Example 1-3 inclusive.

From Tables IV-A and IV-B it may be seen that predicted water removal resulting from control of the rate of rotation of motor 148, represented as cumulative milliliters of water predicted to be removed within the physician pre-set total time for the treatment, is close to the actual weight loss and shows a maximum percent deviation of about 8%. This degree of accuracy is better than that normally attained in clinical hemodialysis in modern clinics in the United States.

a portion of a kidney spent dialysate removal line, first and second cylinder units having means for separating each said cylinders(s) into two chambers as said means moves between the ends of said cylinder, said first and second units each having valves and interconnected switching means effective to cause concurrently one of said units to fill with fresh dialysate as spent dialysate is discarded while the other said unit fills with spent dialysate as fresh dialysate is supplied to said kidney and to alternate functions after said valves are switched at the same time, and ultrafiltrate removal means connected between one of said dialysate lines and said dialysate drain line effective to withdraw dialysate from said line and transfer same to said dialysate drain line, and means for actuating said ultrafiltrate removal means independently of the means actuating said first and said second cylinder units and remotely located control means for controlling said ultrafiltrate removal means, and a degassifier located in the spent dialysate delivery line adjacent to the chamber of said cylinder unit to be filled therewith, said below atmospheric pressure portion including a portion of a kidney spent dialysate removal line, an artificial kidney having a membrane capable of permitting simultaneous dialysis and ultrafiltration of blood and a pair of inlet and outlet blood ports and a pair of inlet and outlet dialysate ports, pressure reducing means in the fresh dialysate supply line to said artificial kidney adjacent to said dialysate inlet port thereof, and pressure increasing means in the spent dialysate removal line from said kidney adjacent to said dialysate outlet port thereof.

TABLE IV-A

|  | Blood Flow Rate ML/MIN. | Dialysate Flow Rate ML/MIN. | Time | Predicted UF-ML. | Actual UF-ML | Percent Deviation | Kidney CDAK ™ No. |
|---|---|---|---|---|---|---|---|
| Clinic No. 1 |  |  |  |  |  |  |  |
| Treatment No. 1 | 230 avg. | 500 | 4 hrs. 5 min. | 1288 | 1408 | −8.11 | 5 |
| Treatment No. 2 | 230 avg. | 500 | 3 hrs. 37 min. | 1758 | 1846 | −5.0 | 7 |
| Treatment No. 3 | 230 avg. | 500 | 4 hrs. 35 min. | 2116 | 1966 | +7.63 | 7 |
| Treatment No. 4 | 230 avg. | 500 | 3 hrs. 55 min. | 2583 | 2780 | −7.09 | 7 |
| Treatment No. 5 | 230 avg. | 500 | 4 hrs. 3 min. | 3544 | 3488 | +1.61 | 5 |

TABLE IV-B

|  | Blood Flow Rate ML/MIN. | Dialysate Flow Rate ML/MIN. | Time | Predicted UF-ML. | Actual UF-ML | Percent Deviation | Kidney CDAK ™ No. |
|---|---|---|---|---|---|---|---|
| Clinic No. 2 |  |  |  |  |  |  |  |
| Treatment No. 1 | 215 | 451 | 4 hrs. 26 min. | 3318 | 3230 | +3 | 7 |
| Treatment No. 2 | 250 | 452 | 4 hrs. 30 min. | 3943 | 3890 | +1 | 7 |
| Treatment No. 3 | 200 | 457 | 3 hrs. 0 min. | 3303 | 3460 | −4.5 | 7 |
| Treatment No. 4 | 210 | 459 | 3 hrs. 22 min. | 2614 | 2695 | −3.0 | 7 |

We claim:

1. An improved closed dialysate circuit for use in hemodialysis comprising an above atmospheric pressure portion comprising dialysate supply and removal means and ultrafiltrate removal means and below atmospheric pressure portion comprising a hemodialyzer, said above atmospheric pressure portion including a dialysate supply line and a dialysate drain line, a portion of a kidney fresh dialysate supply line and 2. An improved dialysate circuit in accordance with claim 1 wherein each said first and second cylinder is separated into two chambers by a double-acting piston attached to a common driving means for reciprocating said pistons.

3. An improved dialysate circuit in accordance with claim 2 wherein said (fresh dialysate) ultrafiltrate removal means is a double-acting piston and cylinder unit having valves and interconnected switching means effective to withdraw fresh dialysate from said fresh dialysate supply line and (trasnfer) transfer same to said dialysate drain line and said actuating means is controllable to vary the quantity transferred.

4. An improved dialysate circuit in accordance with claim 1 wherein each said first and second cylinder is separated into two chambers by a diaphragm.

5. An improved dialysate circuit in accordance with claim 1 wherein means is provided to connect said fresh dialysate supply line directly to the spent dialysate line at a location between said pressure reducing means and the fresh dialysate inlet port of said kidney.

6. An improved dialysis circuit in accordance with claim 1 wherein said pressure reducing means is a back pressure regulator.

7. An improved dialysate circuit in accordance with claim 1 wherein said pressure increasing means is pump means.

8. A method for automatically controlling ultrafiltration during hemodialysis in a single pass system which comprises the steps of
  (1) providing a closed circuit having an artificial kidney below atmospheric pressure portion thereof and means for supplying fresh and removing spent dialysate from said kidney and for removing fresh dialysate from said circuit in an above atmospheric pressure portion of said circuit,
  (2) supplying blood to and from said kidney,
  (3) supplying fresh dialysate from means in said above atmospheric pressure portion of said circuit to said kidney,
  (4) withdrawing degassed dialysate from said closed circuit at a location in said above atmospheric pressure portion of said circuit at a rate pre-selected for removal of water from said blood,
  (5) returning spent dialysate from said kidney to said spent dialysate removal means, and
  (6) raising the pressure on said spent dialysate to a pressure higher than the pressure on said spent dialysate at the kidney exit port and to a pressure at least as high as the pressure on said fresh dialysate in said fresh dialysate supply means at a location intermediate said kidney and said spent dialysate removal means, and
  (7) removing gas bubbles from the pressurized spent dialysate solution produced in step 6 prior to returning the resultant gas-free spent dialysate to said spent dialysate removal means, and
  (8) controlling the rate of water removal from said blood in said kidney by controlling the rate of withdrawal of dialysate in the said above atmospheric pressure portion of said circuit.

9. A method in accordance with claim 8 wherein the pressure in said above atmospheric pressure portion of said closed circuit is maintained in the range of about 1 to about 20 psi above atmospheric pressure.

10. A method in accordance with claim 9 wherein the pressure on said supply dialysate in said dialysate supply means is maintained in the range of about 2 to about 7 psi above atmospheric pressure, and the pressure on spent dialysate resulting from step 6 is maintained in the range of about 2 to about 10 psi greater than the pressure on said supply dialysate.

11. A method in accordance with claim 8 wherein the pressure in said below atmospheric pressure portion of said circuit is in the range of about 260 to about 720 mm of mercury below atmospheric pressure.

12. An improved dialysate circuit in accordance with claim 1 wherein said ultrafiltrate removal means is connected into said fresh dialysate supply line.

13. A method in accordance with claim 8 wherein said dialysate is withdrawn from a portion of said fresh dialysate supply line that is located within said above atmospheric pressure portion of said circuit.

* * * * *